(12) United States Patent
Kagawa et al.

(10) Patent No.: US 8,394,769 B2
(45) Date of Patent: Mar. 12, 2013

(54) ANTI-HYPERTENSIVE AGENT

(75) Inventors: Kyoichi Kagawa, Ibaraki (JP); Chizuko Fukuhama, Ibaraki (JP); Hiroaki Fujino, Ibaraki (JP); Junnei Hidasa, Ibaraki (JP)

(73) Assignee: MG Pharma Inc., Osaka (JP)

(*) Notice: Subject to any disclaimer, the term of this patent is extended or adjusted under 35 U.S.C. 154(b) by 343 days.

(21) Appl. No.: 12/671,953

(22) PCT Filed: Aug. 7, 2008

(86) PCT No.: PCT/JP2008/064247
§ 371 (c)(1),
(2), (4) Date: Feb. 3, 2010

(87) PCT Pub. No.: WO2009/020189
PCT Pub. Date: Feb. 12, 2009

(65) Prior Publication Data
US 2011/0166073 A1 Jul. 7, 2011

(30) Foreign Application Priority Data
Aug. 7, 2007 (JP) ................................ 2007-204929

(51) Int. Cl.
*A61K 38/04* (2006.01)
*A61K 38/06* (2006.01)
*A61K 38/00* (2006.01)
*C07K 5/00* (2006.01)
*C07K 7/00* (2006.01)
*A61P 9/12* (2006.01)

(52) U.S. Cl. ......... 514/15.7; 530/330; 530/331; 514/1.1

(58) Field of Classification Search .................. 530/330, 530/331; 514/1.1, 15.7
See application file for complete search history.

(56) References Cited

U.S. PATENT DOCUMENTS
5,958,885 A 9/1999 Kagawa et al.

FOREIGN PATENT DOCUMENTS

| CN | 199464 | | 7/2007 |
|---|---|---|---|
| DE | 101 33 576 | * | 1/2003 |
| JP | 09-255698 A | | 9/1997 |
| JP | 11263733 | | 9/1999 |
| JP | 2002-80496 A | | 3/2002 |
| WO | 01/68674 | | 9/2001 |
| WO | 2004/044004 | * | 5/2004 |
| WO | 2006/052031 | | 5/2006 |

OTHER PUBLICATIONS

Katakuse et al., 1984, Secondary Ion Mass Spectra of Tryptic Peptides of Human Hemoglobin Chains, Biomedical Mass Spectrometry, 11(8): 386-391.*
Kagawa, K et al., Globin Digest, Acidic Protease Hydrolysate, Inhibits Dietary Hypertriglyceridemia and Val-Val-Tyr-Pro, One of Its Constituents, Possesses Most Superior Effect, Life Sciences, vol. 58, No. 20, Jan. 1, 1996, pp. 1745-1755.
Katakuse, I et al., Secondary ion mass spectra of tryptic peptides of human hemoglobin chains, Biomedical Mass Spectrometry Aug. 1984, vol. 11, No. 8, pp. 386-391.
Mito Kazue et al., Antihypertensive effect of angiotensin I-converting enzyme inhibitory peptides derived from hemoglobin, European Journal of Pharmacology, vol. 304, No. 1-3, 1996, pp. 93-98.
Zhao, Q Y et al., Inhibition and Inhibition Kinetics of Angiotensin Converting Enzyme Activity by Hemorphins, Isolated from a Peptic Bovine Hemoglobin Hydrolysate, Biochemical and Biophysical Research Communications, vol. 204, No. 1, Oct. 15, 1994, pp. 216-223.
Yu, Y et al., Isolation and characterization of angiotensin I-converting enzyme inhibitory peptides derived from porcine hemoglobin, Peptides, vol. 27, No. 11, Nov. 1, 2006, pp. 2950-2956.
European Search Report for Appln. No. 08 82 7111, dated Aug. 31, 2010.
Yoshihara, F., et al., Plasma atrial natriuretic peptide concentration inversely correlates with left atrial fibrillation. Plasma ANP as a possible biochemical marker to predict the outcome of the maze procedure. J Am Coll Cardiol, 39, 288-294, 2002.
Horio, T., et al., Gene expression, secretion, and autocrine action of C-type natriuretic peptide in cultured adult rat cardiac fibroblasts, Endocrinology, 144, 2279-2284, 2003.
Takami, Y., et al., Diagnostic and prognostic value of plasma brain natriuretic peptide in non-dialysis-dependent chronic renal failure, Am J Kidney Dis, 44, 420-428, 2004.
Yoshihara, F., et al., Possible involvement of oxidative stress in hypoxia-induced adrenomedullin secretion in cultured rat cardiomyocytes, Eur J Pharmacol, 436, 1-6, 2002.
Matsui, T., Production of Hypotensive Peptide, SVY, from 7S Globulin of Soybean Protein and Its Physiological Functions, Soybean protein research, 6, 73-77, 2003, abstract only.

* cited by examiner

*Primary Examiner* — Amber D. Steele
(74) *Attorney, Agent, or Firm* — Roylance, Abrams, Berdo & Goodman, L.L.P.

(57) ABSTRACT

The present invention provides an anti-hypertensive agent. The anti-hypertensive agent of the present invention contains, as an active ingredient, at least one peptide selected from the group consisting of peptides originally derived from globin proteolysate, each of which consists of one of the following amino acid sequences (1) to (6), or a globin proteolysate containing at least one of the peptides: (1) Val-Val-Tyr-Pro (SEQ ID: NO. 1); (2) Trp-Gly-Lys-Val-Asn (SEQ ID: NO. 2); (3) Trp-Gly-Lys-Val (SEQ ID: NO. 3); (4) Trp-Gly-Lys (SEQ ID: NO. 4); (5) Ala-Ala-Trp-Gly-Lys (SEQ ID: NO. 5); and (6) Phe-Glu-Ser (SEQ ID: NO. 6).

12 Claims, 8 Drawing Sheets

US 8,394,769 B2

ANTI-HYPERTENSIVE AGENT

TECHNICAL FIELD

The present invention relates to an anti-hypertensive agent comprising a peptide as an active ingredient.

BACKGROUND ART

Hypertension and diseases caused by hypertension are the leading cause of death in the world. Globally, one out of four adults, which correspond to about 100 million people, are said to suffer from these conditions. In particular, the risk of developing cardiovascular complications caused by hypertension is 2 to 4 times higher for diabetic patients than for non-diabetic patients. The International Diabetes Federation advocates the necessity of strict blood pressure control.

However, in spite of various treatments, blood pressure has not been reduced to the desired values in approximately 70% of hypertensive patients and in approximately 90% of patients suffering from both diabetes and hypertension. Although hypertension is recognized as a main risk factor for cardiovascular diseases such as cerebral apoplexy and myocardial infarction, it is not well known that insufficient blood pressure control (particularly, masked hypertension) is a more serious risk factor. In fact, it is reported that about 90% of hypertensive patients with cerebral infarction have been treated for hypertension before the onset of cerebral infarction. This precisely indicates that insufficient anti-hypertensive treatment causes cerebral apoplexy. The result of another clinical test reveals that the reduction of systolic blood pressure by only 10 mmHg can reduce the onset of cerebral apoplexy by about 40%. This result also indicates that "10 mmHg increase" in blood pressure is a very high risk factor.

Pharmaceuticals currently used for treating hypertension can be roughly classified into the following 6 types according to their mechanism of action:
(A) diuretics;
(B) calcium antagonists;
(C) angiotensin-receptor antagonists;
(D) angiotensin-converting enzyme inhibitors;
(E) beta blockers; and
(F) alpha blockers Recently, anti-hypertensive peptides, which have an action of reducing blood pressure, have been attracting attention. Specific examples of anti-hypertensive peptides include biogenic peptides such as natriuretic peptides (ANP, BNP, CNP) (see, for example, Non-Patent Documents 1 to 3) and adrenomedullin (see Non-Patent Document 4); an enzymatic albumin hydrolysate Arg-Pro-Leu-X-Pro-Trp (wherein X is His, Lys, or Arg) (SEQ ID: NO. 7) (see Patent Document 1); and an enzymatic hydrolysate of soybean protein (see Non-Patent Document 5).

Presently, lifestyle habits are considered to have a strong influence on the onset of hypertension and dietary habits are continually being modified. Therefore, peptides derived from egg white or soybean, as described in Patent Document 1 or Non-Patent Document 5, are considered to be highly useful because these peptides are safe and can be produced by the ingestion and subsequent digestion of egg white or soybean.
Non-Patent Document 1: F. Yoshihara et al., Plasma atrial natriuretic peptide concentration inversely correlates with left atrial collagen volume fraction in patients with atrial fibrillation. Plasma ANP as a possible biochemical marker to predict the outcome of the maze procedure. J Am Coll Cardiol, 39, 288-294, 2002
Non-Patent Document 2: T. Norio et al., Gene expression and secretion, and autocrine action of C-type natriuretic peptide in cultured adult rat cardiac fibroblasts. Endocrinology, 144, 2279-2284, 2003
Non-Patent Document 3: Y. Takami et al., Diagnostic and prognostic value of plasma brain natriuretic peptide in non-dialysis-dependent chronic renal failure. Am J Kidney Dis, 44, 419-429, 2004
Non-Patent Document 4: F. Yoshihara et al., Possible involvement of oxidative stress in hypoxia-induced adrenomedullin secretion in cultured rat cardiomyocytes. Eur J Pharmacol, 436, 1-6, 2002
Non-Patent Document 5: Toshiro Matsui, "Production of Hypotensive Peptide, SVY, from 7S Globulin of Soybean Protein and Its Physiological Functions", Soybean protein research, 6, 73-77, 2003
Patent Document 1: Japanese Unexamined Patent Publication No. 2002-80496

DISCLOSURE OF THE INVENTION

Problem to be Solved by the Invention

An object of the present invention is to provide an anti-hypertensive agent comprising a low molecular weight peptide as an active ingredient, and particularly a peptide derived from a globin proteolysate.

Since the risk of developing cardiovascular complications caused by hypertension is 2 to 4 times higher for diabetic patients than for non-diabetic patients, another object of the present invention is to provide an anti-hypertensive agent that has antidiabetic effect in addition to a blood pressure-lowering effect and is particularly suitable for ameliorating hypertension in diabetic patients or in prediabetic patients.

Means for Solving the Problem

The present inventors conducted extensive research to achieve the above objects. As a result, the inventors found that a globin proteolysate, which has an inhibiting effect on the increase in blood glucose levels or an insulin secretion-enhancing effect and is known to be effective for treating diabetics (see WO 2006/052031 A1), and a peptide, which is contained in the globin proteolysate and comprises an amino acid sequence Val-Val-Tyr-Pro (SEQ ID: NO. 1), Trp-Gly-Lys-Val-Asn (SEQ ID: NO. 2), Trp-Gly-Lys-Val (SEQ ID: NO. 3), Trp-Gly-Lys (SEQ ID: NO. 4), Ala-Ala-Trp-Gly-Lys (SEQ ID: NO. 5), or Phe-Glu-Ser (SEQ ID: NO. 6), can produce a blood pressure-lowering effect in hypertensive patients. The inventors thus ascertained that these substances are useful as bioactive peptides to achieve the above objects.

The present inventors further found that among the above peptides, a peptide comprising an amino acid sequence Val-Val-Tyr-Pro (SEQ ID: NO. 1) and a globin proteolysate containing this peptide have an inhibiting effect on the increase in blood glucose levels or an insulin secretion-enhancing effect as described in WO 2006/052031 A1, and are therefore suitable for use as a bioactive peptide for ameliorating hypertension in diabetic patients or prediabetic patients.

The present invention has been accomplished based on the above findings. Thus, the present invention provides the following items:
(I) Anti-Hypertensive Agent
(I-1) An anti-hypertensive agent comprising, as an active ingredient, at least one peptide selected from the group consisting of peptides originally derived from globin proteolysate, each of which consists of one of the following amino acid sequences (1) to (6), or a globin proteolysate containing at least one of the peptides:

```
(1) Val-Val-Tyr-Pro,       (SEQ ID: NO. 1)
(2) Trp-Gly-Lys-Val-Asn,   (SEQ ID: NO. 2)
(3) Trp-Gly-Lys-Val,       (SEQ ID: NO. 3)
(4) Trp-Gly-Lys,           (SEQ ID: NO. 4)
(5) Ala-Ala-Trp-Gly-Lys,   (SEQ ID: NO. 5)
and
(6) Phe-Glu-Ser.           (SEQ ID: NO. 6)
```

(I-2) The anti-hypertensive agent according to (I-1), wherein the active ingredient is a peptide consisting of an amino acid sequence (1) Val-Val-Tyr-Pro (SEQ ID NO. 1), or a globin proteolysate containing the peptide.

(I-3) The anti-hypertensive agent according to (I-1) or (I-2), which is orally administered to a mildly hypertensive patient.

(I-4) The anti-hypertensive agent according to (I-2), which is administered to a hypertensive patient with a disease caused by hyperglycemia or in a pre-disease state.

(I-5) The anti-hypertensive agent according to any one of (I-1) to (I-4), which is administered by the oral route every day in an amount such that the total dose of at least one of the peptides of amino acid sequences (1) to (6) is 1 to 500 mg/adult/day, or the dose of the globin proteolysate containing at least one of the peptides is 0.1 to 5 g/adult/day.

(II) Method of Ameliorating Hypertension or Preventing or Treating a Disease Caused by Hypertension (II-1) A method of ameliorating hypertension or preventing or treating a disease caused by hypertension, comprising administering to a hypertensive patient an anti-hypertensive agent comprising, as an active ingredient, at least one peptide selected from the group consisting of peptides originally derived from globin proteolysate, each of which consists of one of the following amino acid sequences (1) to (6), or a globin proteolysate containing at least one of the peptides:

```
(1) Val-Val-Tyr-Pro,       (SEQ ID: NO. 1)
(2) Trp-Gly-Lys-Val-Asn,   (SEQ ID: NO. 2)
(3) Trp-Gly-Lys-Val,       (SEQ ID: NO. 3)
(4) Trp-Gly-Lys,           (SEQ ID: NO. 4)
(5) Ala-Ala-Trp-Gly-Lys,   (SEQ ID: NO. 5)
and
(6) Phe-Glu-Ser.           (SEQ ID: NO. 6)
```

(II-2) A method of ameliorating hypertension or preventing or treating a disease caused by hypertension, comprising administering to a hypertensive patient with a disease caused by hyperglycemia an anti-hypertensive agent comprising, as an active ingredient, a peptide consisting of an amino acid sequence (1) Val-Val-Tyr-Pro (SEQ ID: NO. 1) or a globin proteolysate containing the peptide.

(II-3) The method according to (II-1) or (II-2), wherein the anti-hypertensive agent is orally administered to a mildly hypertensive patient.

(II-4) The method according to (II-2), wherein the anti-hypertensive agent is administered to a hypertensive patient with a disease caused by hyperglycemia or in a pre-disease state.

(II-5) The method according to any one of (II-1) to (II-4), wherein the anti-hypertensive agent is administered by the oral route every day in an amount such that the total dose of at least one of the peptides of amino acid sequences (1) to (6) is 1 to 500 mg/adult/day or the dose of the globin proteolysate containing at least one of the peptides is 0.1 to 5 g/adult/day.

(III) Use of Peptide and Globin Proteolysate (III-1) Use of at least one peptide selected from the group consisting of peptides originally derived from globin proteolysate, each of which consists of one of the following amino acid sequences (1) to (6), or a globin proteolysate containing at least one of the peptides to produce an anti-hypertensive agent:

```
(1) Val-Val-Tyr-Pro,       (SEQ ID: NO. 1)
(2) Trp-Gly-Lys-Val-Asn,   (SEQ ID: NO. 2)
(3) Trp-Gly-Lys-Val,       (SEQ ID: NO. 3)
(4) Trp-Gly-Lys,           (SEQ ID: NO. 4)
(5) Ala-Ala-Trp-Gly-Lys,   (SEQ ID: NO. 5)
and
(6) Phe-Glu-Ser.           (SEQ ID: NO. 6)
```

(III-2) Use of a peptide consisting of an amino acid sequence (1) Val-Val-Tyr-Pro (SEQ ID: NO. 1), or a globin proteolysate containing the peptide to produce an anti-hypertensive agent for a hypertensive patient with a disease caused by hyperglycemia.

(III-3) A peptide or a globin proteolysate used to ameliorate hypertension or prevent or treat a disease caused by hypertension, the peptide being at least one peptide selected from the group consisting of peptides originally derived from globin proteolysate, each of which consists of one of the following amino acid sequences (1) to (6), or a globin proteolysate containing at least one of the following peptides:

```
(1) Val-Val-Tyr-Pro,       (SEQ ID: NO. 1)
(2) Trp-Gly-Lys-Val-Asn,   (SEQ ID: NO. 2)
(3) Trp-Gly-Lys-Val,       (SEQ ID: NO. 3)
(4) Trp-Gly-Lys,           (SEQ ID: NO. 4)
(5) Ala-Ala-Trp-Gly-Lys,   (SEQ ID: NO. 5)
and
(6) Phe-Glu-Ser.           (SEQ ID: NO. 6)
```

(III-4) A peptide consisting of an amino acid sequence (1) Val-Val-Tyr-Pro (SEQ ID: NO. 1) or a globin proteolysate containing the peptide, which is used in a method of ameliorating hypertension in a hypertensive patient with a disease caused by hyperglycemia or in a method of preventing or treating a disease caused by hypertension in the patient.

Effect of the Invention

The present invention provides an anti-hypertensive agent that decreases blood pressure to ameliorate hypertension. In particular, an anti-hypertensive agent of the present invention that comprises a peptide consisting of an amino acid sequence (1) Val-Val-Tyr-Pro (SEQ ID: NO. 1) or a globin proteolysate containing this peptide has an inhibiting effect on the increase in blood glucose levels or an insulin secretion-promoting effect as well as a blood pressure-lowering effect, and therefore can be more effectively used for hypertensive patients with diabetes or prediabetes.

BEST MODE FOR CARRYING OUT THE INVENTION

A feature of the anti-hypertensive agent of the present invention is to comprise at least one peptide selected from the group consisting of: a peptide consisting of an amino acid sequence (1) Val-Val-Tyr-Pro (SEQ ID: NO. 1) (hereinafter simply referred to as "peptide (VVYP)"); a peptide consisting of an amino acid sequence (2) Trp-Gly-Lys-Val-Asn (SEQ ID: NO. 2) (hereinafter simply referred to as "peptide (WGKVN)"); a peptide consisting of an amino acid sequence (3) Trp-Gly-Lys-Val (SEQ ID: NO. 3) (hereinafter simply referred to as "peptide (WGKV)"); a peptide consisting of an amino acid sequence (4) Trp-Gly-Lys (SEQ ID: NO. 4) (hereinafter simply referred to as "peptide (WGK)"); a peptide consisting of an amino acid sequence (5) Ala-Ala-Trp-Gly-Lys (SEQ ID: NO. 5) (hereinafter simply referred to as "peptide (AAWGK)); a peptide consisting of an amino acid sequence (6) Phe-Glu-Ser (SEQ ID: NO. 6) (hereinafter simply referred to as "peptide (FES)"); or a globin proteolysate containing at least one of the above peptides.

All the above peptides can be prepared by chemical synthesis using known peptide synthesis methods. Examples of peptide synthesis methods include the azide method, acid chloride method, acid anhydride method, mixed acid anhydride method, DCC method, activated ester method, carboimidazole method, oxidation-reduction method, DCC-additive (HOME, HOBt, HOSu) methods ("The Peptide" Vol. 1 (1966), Schreder & Luhke, Academic Press, New York, USA; or "Peptide Gosei", Izumiya et al., Maruzen (1975), etc.), and the like. Such peptide synthesis methods may be performed by either solid-phase or liquid-phase methods.

In such peptide synthesis methods, amino acids having side-chain functional groups, e.g., tyrosine and threonine, preferably have protected side chain functional groups. Examples of protective groups that can be used include known protective groups such as benzyloxycarbonyl (Cbz-), t-butoxycarbonyl (Boc-) and benzyl (Bz-) groups. Such protective groups can be removed according to known methods during the peptide synthesis process of the present invention.

Since all the above peptides are contained in hydrolysates of globin protein (hereinafter referred to as "globin proteolysate"), such as hemoglobin and myoglobin, the peptides can also be obtained by isolation and purification from the globin proteolysate. Isolation or purification of the peptides can also be performed using, as the starting material, a hydrolysate of a protein other than globin, such as a hydrolysate of a fish meat protein, fish powder, or corn protein (zein). When an animal protein is used as the globin protein, the source of the protein is not particularly limited. For example, the blood of a wide variety of animals, such as cows, pigs, sheep, humans, and horses, can be used. Meat containing large amounts of myoglobin, such as the meat of domesticated animals or fish meat, can also be used as the globin protein source.

Hydrolysis of globin protein and other procedures can be performed according to the methods described in WO89/06970. The hydrolysis is usually performed using one or more hydrolases, such as acid proteases, neutral proteases, or alkaline proteases.

More specifically, a method for hydrolyzing a globin protein comprises, for example, dispersing a globin protein-containing material in water to a concentration of 5 to 30% by weight (solids content), adjusting the pH with an acid or base to the optimum pH for a protease, adding a protease all at once or gradually, and reacting the enzyme at a temperature of 20 to 70° C. for 3 to 48 hours.

Known purification methods for proteins or peptides can be used as the method of isolating the peptide of the present invention from the thus obtained globin proteolysate. For example, salting out, dialysis, ion exchange resin, ultrafiltration, reverse phase chromatography, or like methods can be used singly or, if necessary, in a suitable combination thereof, whereby a fraction containing the peptide (VVYP; SEQ ID NO:1), peptide (WGKVN; SEQ ID NO:2), peptide (WGKV; SEQ ID NO:3), peptide (WGK; SEQ ID NO:4), peptide (AAWGK; SEQ ID NO:5), or peptide (FES; SEQ ID NO:6) can be obtained and the peptide can further be isolated from the fraction. Among these purification methods, reverse phase chromatography is preferably performed either under acidic conditions, or under acidic conditions and neutral conditions.

The amount of protein in each fraction can be measured by a known protein assay method, such as the ninhydrin method. The amino acid sequence of a peptide contained in the selected fraction can be identified by a known method (amino acid analysis) to ascertain the presence of the peptide (VVYP; SEQ ID NO:1), peptide (WGKVN; SEQ ID NO:2), peptide (WGKV; SEQ ID NO:3), peptide (WGK; SEQ ID NO:4), peptide (AAWGK; SEQ ID NO:5), or peptide (FES; SEQ ID NO:6) which are the target peptides of the invention. The anti-hypertensive agent of the invention may contain at least one of the peptides having been isolated and purified by a method as described above. Alternatively, a crude product containing at least one of the peptides may be incorporated in the anti-hypertensive agent, as long as the crude product has a blood pressure-lowering effect. Examples of such crude products include globin proteolysates containing the above peptides, and fractions thereof.

The anti-hypertensive agent of the present invention may consist of at least one of the above peptides or a crude product containing at least one of the above peptides (a globin proteolysate or a fraction thereof). However, the anti-hypertensive agent is typically prepared using a pharmacologically acceptable carrier or an additive in addition to the active ingredient. When a pharmacologically acceptable carrier or an additive is used with the active ingredient to prepare the anti-hypertensive agent, the amount of peptide is not particularly limited as long as it is an amount effective enough to have a blood pressure-lowering effect.

The peptide (VVYP; SEQ ID NO:1) or a globin proteolysate containing the peptide has an inhibiting effect on the increase in blood glucose levels or an insulin secretion-enhancing effect, in addition to a blood pressure-lowering effect. Accordingly, when the anti-hypertensive agent of the present invention contains, as an active ingredient, the peptide (VVYP; SEQ ID NO:1) or a globin proteolysate containing the peptide, the amount of peptide in the anti-hypertensive agent is preferably an amount effective enough to have a blood pressure-lowering effect as well as an inhibiting effect on the increase in blood glucose levels or an insulin secretion-enhancing effect.

The carrier to be incorporated into the anti-hypertensive agent of the present invention can be appropriately selected, according to the dosage form of the pharmaceutical preparation, from excipients, diluents, binders, humectants, disintegrators, disintegration inhibitors, absorbefacients, lubricants, solubilizers, buffers, emulsifiers, suspending agents, and the like. The additive can be appropriately selected, according to the dosage form of the pharmaceutical preparation, from stabilizers, preservatives, buffers, isotonic agents, chelating agents, pH adjusters, surfactants, colorants, aroma chemicals, flavorings, sweeteners, and the like that are commonly used.

The unit dosage form of the anti-hypertensive agent can be appropriately selected from a variety of forms according to the administration route, and these forms can be generally classified into oral agents, transpulmonary agents, transnasal agents, sublingual agents, parenteral agents (injections, drips), and the like. The anti-hypertensive agent can be prepared according to known methods into solid dosage forms such as tablets, pills, powdered drugs, powders, granules, and capsules, or liquid dosage forms such as solutions, suspensions, emulsions, syrups, and elixirs. By the addition of an appropriate carrier, the anti-hypertensive agent may be prepared as a dried product that can be converted into a liquid form before use. The anti-hypertensive agent can be prepared into such dosage forms according to known methods.

The anti-hypertensive agent of the invention may contain one or more of the peptides in a total amount of typically about 0.001 to about 80 wt. %, preferably about 0.1 to about 50 wt. %, and more preferably about 0.1 to about 10 wt. %.

The dose of the anti-hypertensive agent thus obtained can be appropriately selected according to the purpose (exhibition of a blood pressure-lowering effect, or exhibition of an inhibiting effect on the increase in blood glucose levels or an insulin secretion-enhancing effect as well as a blood pressure-lowering effect); the method of administering the anti-hypertensive agent; dosage form; age, body weight, symptoms (severity of disease) of the patient; and other factors. More specifically, the dose of the peptide of the present invention (the total dose of the peptides when two or more peptides are used) may be in the range of about 1 to about 500 mg, preferably about 2 to about 100 mg, per adult per day. The dose of the globin proteolysate of the present invention may be in the range of about 0.1 to about 5 g, preferably about 0.5 to about 3 g, per adult per day.

The anti-hypertensive agent does not have to be administered in a single dose, and can be administered in 2 to 4 divided doses per day. The anti-hypertensive agent can be prepared into various forms and administered by a route suitable for the dosage form. For example, the anti-hypertensive agent in an injectable form can be administered intravenously, intramuscularly, subcutaneously, intracutaneously, intraperitoneally, etc. The anti-hypertensive agent in a solid form can be administered orally etc. Oral administration is preferable.

As shown in the Experimental Examples below, the anti-hypertensive agent of the present invention has a blood pressure-lowering effect in hypertensive patients to ameliorate hypertension. Therefore, the anti-hypertensive agent of the present invention is also effective as a composition for preventing or treating various diseases caused by hypertension.

Table 1 shows a classification of hypertension prescribed by The Japanese Society of Hypertension and WHO/ISH.

TABLE 1

| Classification | Systolic blood pressure (mmHg) | | Diastolic blood pressure (mmHg) |
|---|---|---|---|
| Optimum blood pressure | <120 | and | <80 |
| Normal blood pressure | <130 | and | <85 |
| High normal blood pressure | 130 to 139 | or | 85 to 89 |
| Mild hypertension | 140 to 159 | or | 90 to 99 |

TABLE 1-continued

| Classification | Systolic blood pressure (mmHg) | | Diastolic blood pressure (mmHg) |
|---|---|---|---|
| Moderate hypertension | 160 to 179 | or | 100 to 109 |
| Severe hypertension | ≧180 | or | ≧110 |
| Systolic hypertension | ≧140 | and | <90 |

(2004 Hypertension Treatment Guidelines, edited by The Japanese Society of Hypertension, Committee for Producing Guidelines for Hypertension Treatment)

The target hypertensive patient of the present invention includes patients classified as having mild hypertension, moderate hypertension, severe hypertension, and systolic hypertension according to the above classification of hypertension. Patients with mild hypertension, moderate hypertension, or severe hypertension are preferable. Patients with mild hypertension are particularly preferable. In particular, the peptide (VVYP; SEQ ID NO:1) and a globin proteolysate containing the peptide (VVYP; SEQ ID NO:1) used in the present invention have a diastolic pressure-lowering effect rather than a systolic pressure-lowering effect. Accordingly, hypertensive patients who have a comparatively high diastolic pressure are the most suitable as subjects for using the anti-hypertensive agent of the present invention comprising as an active ingredient the peptide or a globin proteolysate containing the peptide.

The anti-hypertensive agent of the present invention comprising, as an active ingredient, the peptide (VVYP; SEQ ID NO:1) or a globin proteolysate containing the peptide (VVYP; SEQ ID NO:1) has, in addition to a blood pressure-lowering effect, an insulin secretion-enhancing effect resulting from the use of the peptide (VVYP; SEQ ID NO:1) as the active ingredient, thereby ameliorating hyperglycemic conditions caused by a reduction or lack of insulin action and producing a blood glucose-lowering effect. Therefore, the anti-hypertensive agent of the present invention is advantageously used for hypertensive patients with a variety of diseases caused by hyperglycemic conditions resulting from the reduction or lack of insulin action. For example, diabetes and diabetic complications can be mentioned as diseases caused by hyperglycemic conditions. Diabetes that can be the target disease of the present invention includes type II diabetes (non-insulin-dependent diabetes) and type I diabetes (insulin-dependent diabetes). Non-insulin-dependent type II diabetes is preferable. According to the guidelines (1999) of the Japan Diabetes Society, a patient can be diagnosed as diabetic when the patient has at least one of the following blood glucose levels: a casual glucose level of 200 mg/dL or greater, a fasting glucose level of 126 mg/dL or greater, or a 2 hour post-load value of 200 mg/dL or greater after a 75 g oral glucose tolerance test. Further, a patient can be diagnosed as diabetic when positive results according to the above criteria are obtained twice in tests performed on different days, a symptom characteristic of diabetes is observed even once, the concentration of $HbA_{1c}$ (hemoglobin $A_{1c}$) is 6.5% or more, or diabetic retinopathy is observed. The target diabetic patient of the present invention includes prediabetic patients, i.e., patients with impaired glucose tolerance (borderline diabetic patients). A patient can be diagnosed as borderline diabetic when the patient has a fastening glucose level of from 110 to 125 mg/dL, or a 2 hour post-load value of from 140 to 199 mg/dL after the glucose tolerance test.

Diabetic complications refer to systemic or localized diseases directly or indirectly caused by diabetes (preferably non-insulin-dependent type II diabetes) and concurrently occurring with diabetes. Specific examples are diabetic acidosis, diabetic xanthoma, diabetic amyotrophy, diabetic ketosis, diabetic coma, diabetic gastropathy, diabetic gangrene, diabetic ulcer, diabetic complications, diabetic diarrhea, diabetic microangiopathy, diabetic uterosclerosis, diabetic cardiomyopathy, diabetic neuropathy, diabetic nephropathy, bullosis diabeticorum, diabetic cataract, diabetic dermopathy, diabetic scleredema, diabetic retinopathy, necrobiosis lipoidica diabeticorum, diabetic blood circulation disorder, etc.

EXAMPLES

Preparation Examples and Experimental Examples are given below to illustrate the invention in more detail, but the scope of the invention is not limited by these examples. In the following Experimental Examples, "%" represents "percent by weight", unless otherwise specified.

Preparation Example 1

Production of Globin Proteolysate

A method for producing a globin proteolysate using bovine erythrocytes is described below in detail.

250 liters of water was added to 100 kg of fresh bovine erythrocytes to allow sufficient hemolysis. After adjustment of the pH to 2.8 with phosphoric acid, $2.6 \times 10^7$ units of acid protease from *Aspergillus niger* were added to the solution, and the reaction was allowed to proceed at 50° C. for 3 hours.

After the reaction, the reaction mixture was heated at 80° C. for 30 minutes to terminate the reaction. Thereafter, an aqueous suspension of calcium hydroxide was added to the reaction mixture to adjust the pH to 6.5. Then, 10 kg of diatomaceous earth was added, and the mixture was filtered with a filter press. The resulting filtrate was spray-dried to thereby produce 23 kg of a globin proteolysate as a powder. The molecular weight distribution of the obtained globin proteolysate was examined by gel filtration chromatography, which was performed under the following conditions.

<Gel Filtration Chromatography>
Equipment: High-performance liquid chromatograph (manufactured by Shimadzu Corporation, Model "LC-6A")
Column: PolyHYDROXYETHYL A, 5 μm, 9.4×200 mm, manufactured by PolyLC Inc.
Eluate: 50 mM formic acid
Flow rate: 0.5 ml/min
Detection: UV absorption at 221 nm FIG. 1 shows a gel filtration chromatogram of a globin proteolysate obtained by the above gel filtration chromatography.

Preparation Example 2

Fractionation and Purification of Hypotensive Peptides

The peptide (VVYP; SEQ ID NO:1) of the present invention was obtained by subjecting the globin proteolysate obtained in Preparation Example 1 to the following procedures: (1) ion exchange, (2) ultrafiltration, (3) separation by reverse phase column chromatography under acidic conditions, and (4) separation by reverse phase chromatography under neutral conditions.

(1) Ion Exchange
A 10% aqueous solution containing 13.7 g of the globin proteolysate obtained in Preparation Example 1 was introduced to a weakly acidic cation exchange resin (Amberlite $IRC_{50}$, $H^+$ Type, Organo Co., Ltd.). After stirring for 1 hour for adsorption, an unadsorbed fraction was obtained.

(2) Ultrafiltration
The unadsorbed fraction obtained by the above ion exchange was subjected to ultrafiltration using a stirring-ultrafiltration unit (manufactured by Advantec, "UHP 90K") and a ultrafilter membrane (manufactured by Advantec, "UIIH-1", molecular weight cutoff: 1000). The liquid remaining on the ultrafiltration membrane (residual liquid) was collected. The fraction thus obtained was subjected to acid hydrolysis and then quantified by the ninhydrin method. The acid hydrolysis was carried out by placing 1 ml of hydrochloric acid having a final concentration of 6 N into a test tube per 3 to 5 mg of protein, sealing the tube at atmospheric pressure and heating at 110° C. for 22 hours. The ninhydrin method was performed as follows. The pH of the specimen after hydrolysis was adjusted to 5.0 with sodium hydroxide. The specimen was then reacted with a ninhydrin reagent containing a 0.2 M citrate buffer (pH 5.0) at 100° C. for 15 minutes. Absorbance at 570 nm was measured. Separately, aqueous L-leucine solutions (75, 150, 225, and 300 nmol/ml) were subjected to a ninhydrin reaction as standard solutions. A calibration curve was drawn from the measured absorbances, and the amount of amino groups equivalent to L-leucine in the specimen was calculated. Table 2 shows the result of the quantification.

(3) Reverse Phase (Acid) Chromatography
The residual liquid obtained by the ultrafiltration was subjected to reverse phase (acid) chromatography under the following conditions.

<Reverse Phase (Acid) Chromatography>
Equipment: High performance liquid chromatograph (manufactured by Shimadzu Corporation, Model "LC-10A")
Column: SuperPac Pep-S, 15 μm, 22.5×250 mm, manufactured by Pharmacia)
Eluate: Aqueous acetonitrile solution containing 0.1 vol. % trifluoroacetic acid
Gradient: Linear concentration gradient of acetonitrile from 2 to 35 vol. %
Change in the acetonitrile concentration: 1 vol. % increment per min
Flow rate: 5 ml/min
Temperature: 40° C.
Detection: UV absorption at 220 nm
Fractionation time: 53.8 to 54.5 min (Fraction A).

FIG. 2 shows a chromatogram obtained by the above-described reverse phase (acid) chromatography.

The fraction thus obtained was subjected to acid hydrolysis and then quantified by amino acid analysis. The acid hydrolysis was carried out by placing 1 ml of hydrochloric acid (final concentration of 6 N HCl) into a test tube per 3 to 5 mg of protein, sealing the test tube under reduced pressure, and heating at 110° C. for 22 hours. The amino acid analysis was conducted under the following conditions.

<Amino Acid Analysis>
Equipment: High performance liquid chromatograph (manufactured by Shimadzu Corporation, Model "LC-6A")
Column: Shim-pack ISC-07/51504 Na, 7 μm, 4.0×150 mm, manufactured by Shimadzu Corporation
Eluate: Amino acid mobile phase kit (Na type) manufactured by Shimadzu Corporation
Flow rate: 0.3 ml/min
Temperature: 55° C.
Reaction solution 1: Analysis kit OPA reagent manufactured by Shimadzu Corporation
Detection: Fluorescence absorption (Ex 348 nm, Em 450 nm)

The acid-hydrolyzed solution was concentrated to dryness using a rotary evaporator, and further dried under reduced pressure for 12 hours or more to completely remove hydrochloric acid. The resultant was dissolved in 0.2 M citrate buffer (pH 2.2) so that the resulting solution contained each amino acid in an amount of about 100 nmol/ml. This solution was filtered through a 0.45 μm filter, and 10 μl of the filtrate was introduced into a column. Subsequently, an 18-component type H amino acid mixed standard solution (manufactured by Wako Pure Chemical Industries, Ltd.) was diluted 25-fold with 0.2 M citrate buffer (pH 2.2), and 10 μl of the diluted solution was introduced into the column as a standard solution (containing each amino acid in a concentration of 1 nmol/10 μl). The peak areas of the amino acids were calculated and analyzed using Chromatopac C-R4A (manufactured by Shimadzu Corporation). The amounts of the amino acids were calculated based on a comparison of the ratios of the peak areas for the specimen to the peak areas for the standard solution.

(4) Reverse Phase (Neutral) Chromatography

The fraction eluted and fractionated by the above reverse phase (acid) chromatography was further subjected to reverse phase (neutral) chromatography under the following conditions.

<Reverse Phase (Neutral) Chromatography>

Equipment: High performance liquid chromatograph (manufactured by Shimadzu Corporation, Model "LC-10A")
Column: SuperPac Pep-S, 15 22.5×250 mm, manufactured by Pharmacia)
Eluate: Aqueous acetonitrile solution containing 20 mM ammonium acetate buffer (pH 6.5)
Gradient: Linear concentration gradient of acetonitrile from 0 to 25 vol. %
Change in the acetonitrile concentration: 0.5 vol. % increment per min
Flow rate: 5 ml/min
Temperature: 40° C.
Detection: UV absorption at 220 nm
Fractionation time: 45.8 to 51.0 min (Fraction B).

FIG. 3 shows a chromatogram obtained by reverse phase (neutral) chromatography. The obtained fractions were quantified in the same manner as in (3) above, and further identified. The amino acid composition was computed based on the proportion of each amino acid relative to the total amino acid content. The results showed that Fraction B is VVYP (Val-Val-Tyr-Pro; SEQ ID NO:1). These peptides were matched with the amino acid sequences of hemoglobin. The results confirmed that all the peptide sequences were present in hemoglobin. Table 2 shows the results of the quantification.

TABLE 2

| Peptide | Protein weight (g) |
| --- | --- |
| Globin proteolysate | 13.70 |
| Ion exchange + ultrafiltration reverse phase chromatography | 4.24 |
| [Fraction A] | 0.39 |
| [Fraction B] VVYP (SEQ ID NO: 1) | 0.006 |

Preparation Example 3

Fractionation and Purification of Hypotensive Peptide

A 10% aqueous solution containing 100 g of the globin proteolysate prepared in Preparation Example 1 was adsorbed on an open column containing a reverse phase resin (YMC ODS AQ120 S50) (Φ 100 mm×400 mm), and eluted using hydrous ethanol as an eluate, while the concentration of ethanol was increased stepwise by 5 vol. % from 5 to 15 vol. %. Subsequently, the 5 vol. % ethanol-eluted fraction and the 15 vol. % ethanol-eluted fraction were subjected to reverse phase (acid) chromatography under the following conditions.

<Reverse Phase (Acid) Chromatography>

Equipment: High performance liquid chromatograph (Waters Alliance 2695-2996 (manufactured by Waters Corporation))
Column: Nucleosil 5C18 120 Å Φ 4.0×250 mm (manufactured by Chemco Scientific Co., Ltd.)
Eluate: Aqueous acetonitrile solution containing 0.1 vol. % trifluoroacetic acid
Gradient: an acetonitrile concentration of 5 vol. % at 0 to 5 min, a linear concentration gradient of acetonitrile of from 5 to 30 vol. % at 5 to 30 min (change in the acetonitrile concentration: 1 vol. % increment per min)
Flow rate: 0.8 mL/min
Temperature: 40° C.
Detection: UV absorption at 210 nm
Amount introduced: 20 μL FIGS. 4 and 5 show reverse phase chromatograms of the 5 vol. % ethanol-eluted fraction and the 15 vol. % ethanol-eluted fraction.

The peaks obtained in the chromatograms were fractionated. The fractions thus obtained were subjected to acid hydrolysis and then to amino acid analysis according to the method described in Preparation Example 2. The analysis revealed the following. The elution peak at a retention time of 12.55 min in the reverse phase chromatogram (FIG. 4) of the 5 vol. % ethanol-eluted fraction corresponds to the peak of a peptide consisting of the amino acid sequence Phe-Glu-Ser (SEQ ID: NO. 6) (peptide (FES)); and the elution peaks at retention times of 18.16 min and 19.53 min in the reverse phase chromatogram (FIG. 5) of the 15 vol. % ethanol-eluted fraction correspond to the peaks of the peptide consisting of the amino acid sequence Ala-Ala-Trp-Gly-Lys (peptide (AAWGK); SEQ ID NO:5) and the peptide consisting of the amino acid sequence Trp-Gly-Lys-Val-Asn (peptide (WGKVN); SEQ ID NO:2).

Experimental Example 1

Spontaneously hypertensive rats (SHR/Izm, male, 9-week-old, body weight: 266 g, Japan SLC, Inc.) (6 rats) were orally administered with the peptide (VVYP; SEQ ID NO:1) prepared in Preparation Example 2 in a single dose in an amount of 10 mg/kg body weight. Two hours and six hours after the start of administration, the systolic blood pressures of the rats were measured using a non-heating non-invasive blood pressure monitor ("MK-2000", manufactured by Muromachi Kikai Co., Ltd.) by the tail-cuff method without anesthesia (-O-). SHR rats (6 rats) as a control group were orally administered with a solvent (distilled water) in a single dose, and the systolic blood pressures of the rats were measured in a similar manner (-●-). FIG. 6 shows the results. As is clear from FIG. 6, the results verified that the peptide (VVYP; SEQ ID NO:1) of the present invention has a blood pressure-lowering effect.

Experimental Example 2

Spontaneously hypertensive rats (SHR/Izm, male, 14-week-old, body weight at the beginning of administration: 309 g to 359 g, Japan SLC, Inc.) (8 rats) were orally administered with a globin proteolysate containing the peptide (VVYP; SEQ ID NO:1) prepared in Preparation Example 1 in an amount of 1 g/kg body weight for 10 weeks. The systolic blood pressures of the rats were measured using non-heating non-invasive blood pressure manometers ("MK-2000", Muromachi Kikai Co., Ltd.,) by the tail-cuff method without using anesthesia (-O-) every 2 weeks after the start of administration. SHR rats (8 rats) as a control group were orally administered with a solvent (distilled water) in a similar manner for 10 weeks, and the systolic blood pressures of the rats were measured in a similar manner (-●-). FIG. 7 shows the results.

As is clear from FIG. 7, the results show that the globin proteolysate containing the peptide (VVYP; SEQ ID NO:1) of the present invention has a blood pressure-lowering effect.

Experimental Example 3

89 mildly hypertensive patients (systolic blood pressure: 140 to 159 mmHg, or diastolic blood pressure: 90 to 99 mmHg) were divided at random into 2 groups (44 patients and 45 patients). The test group (45 patients) was orally administered with 500 mg of a globin proteolysate containing the peptide (VVYP; SEQ ID NO:1) prepared in Preparation Example 1 three times per day for 10 weeks, whereas the control group (44 patients) was orally administered with the same amount of lactose. Three, six, and ten weeks after the start of administration, the blood pressures (systolic blood pressure and diastolic blood pressure) of the patients were measured, and changes in blood pressures were evaluated.

FIG. 8 shows the results. As shown in FIG. 8, oral administration of the globin proteolysate of the present invention tended to decrease systolic blood pressure, and a significant decrease in diastolic blood pressure was observed from the 6th week after the start of administration (-O-). The difference in systolic blood pressure between the test group and the control group (-●-) in the 10th week after the start of the administration was about 5 mmHg, whereas the difference in diastolic blood pressure therebetween was about 8 mmHg. The above results show that a globin proteolysate containing a peptide (VVYP; SEQ ID NO:1) has a blood pressure-lowering effect in humans.

Experimental Example 4

The following peptides were synthesized according to known methods, based on the amino acid sequences of peptides isolated from the globin proteolysate prepared in Experimental Example 3 and identified. The peptide (WGKV; SEQ ID NO:3) (3) corresponds to a peptide produced by one amino acid deletion at the C terminus from the amino acid sequence of the peptide (WGKVN; SEQ ID NO:2) (2), and the peptide (WGK; SEQ ID NO:4) (4) corresponds to a peptide produced by deleting a further amino acid at the C terminus.

```
(2) Trp-Gly-Lys-Val-Asn      (SEQ ID: NO. 2)
(3) Trp-Gly-Lys-Val          (SEQ ID: NO. 3)
(4) Trp-Gly-Lys              (SEQ ID: NO. 4)
(5) Ala-Ala-Trp-Gly-Lys      (SEQ ID: NO. 5)
(6) Phe-Glu-Ser.             (SEQ ID: NO. 6)
```

Spontaneously hypertensive rats (SHR/Izm, male, 12-week-old, body weight: 285 g, Japan SLC, Inc.) were administered in a single dose with the peptides synthesized above (peptides (2) to (6)) in an amount of 50 mg/kg body weight. Two, four, and six hours after the start of administration, the systolic blood pressures of the rats were measured using a non-heating non-invasive blood pressure monitor ("MK-2000", manufactured by Muromachi Kikai Co., Ltd.) by the tail-cuff method without using anesthesia. Spontaneously hypertensive rats as a control group were orally administered with a solvent (distilled water), and the systolic blood pressures of the rats were measured in a similar manner. FIG. 3 shows the results. As is clear from FIG. 3, the results revealed that all the above peptides have a blood pressure-lowering effect.

TABLE 3

| Amino acid sequence | n | Reduction in blood pressure (mmHg) | | |
| --- | --- | --- | --- | --- |
| | | 2 hours after administration | 4 hours after administration | 6 hours after administration |
| WGKVN | 11 | −16 ± 4** | −12 ± 4* | −14 ± 3** |
| WGKV | 8 | −9 ± 3 | −4 ± 4 | −3 ± 3 |
| WGK | 4 | −3 ± 7 | −23 ± 8** | −15 ± 8 |
| AAWGK | 4 | −7 ± 4 | −8 ± 12 | −4 ± 8 |
| FES | 4 | −15 ± 4* | −13 ± 8 | −15 ± 6 |

*p < 0.05,
**p < 0.01

Experimental Example 5

Safety Test

Male and female ICR mice were orally administered with the peptide (VVYP; SEQ ID NO:1) prepared in Preparation Example 2 in an amount of at least 10 g/kg body weight (the maximum administrable dose), but death was not observed. The results verified that the peptide (VVYP; SEQ ID NO:1) is safe.

SEQUENCE LISTING FREE TEXT

Figure 1:
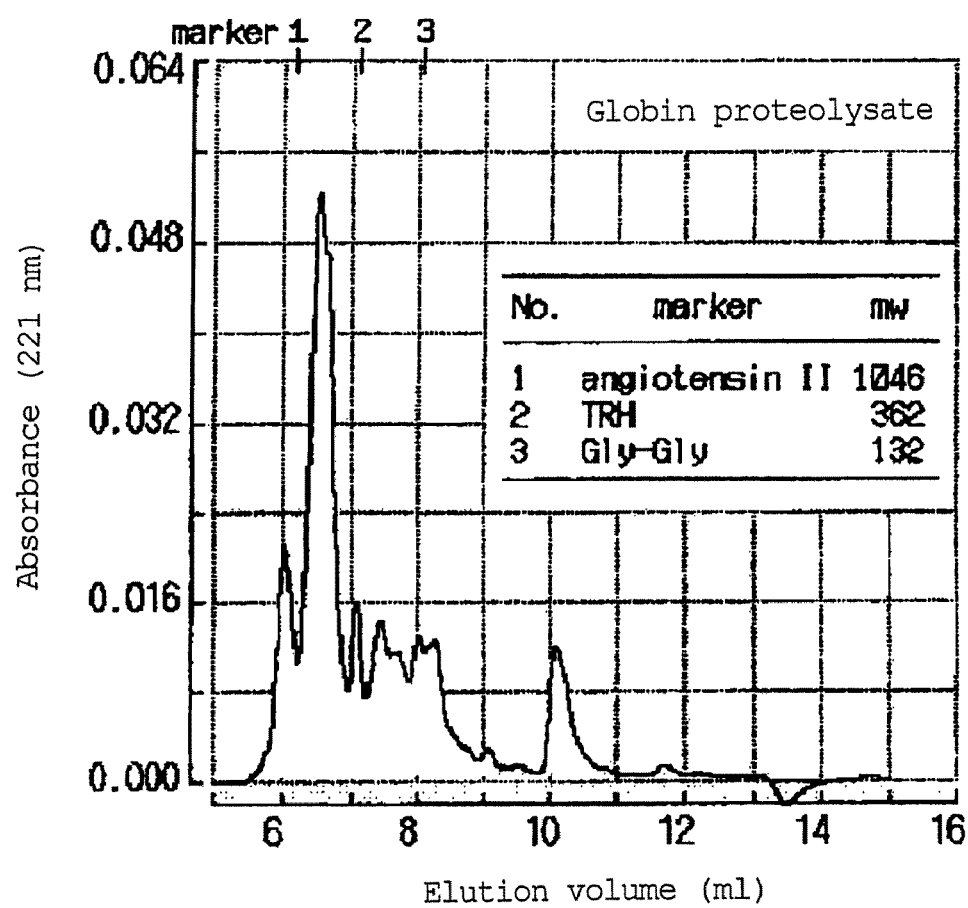
FIG. 1 shows a gel filtration chromatogram of the globin proteolysate (Preparation Example 1).
Figure 2:
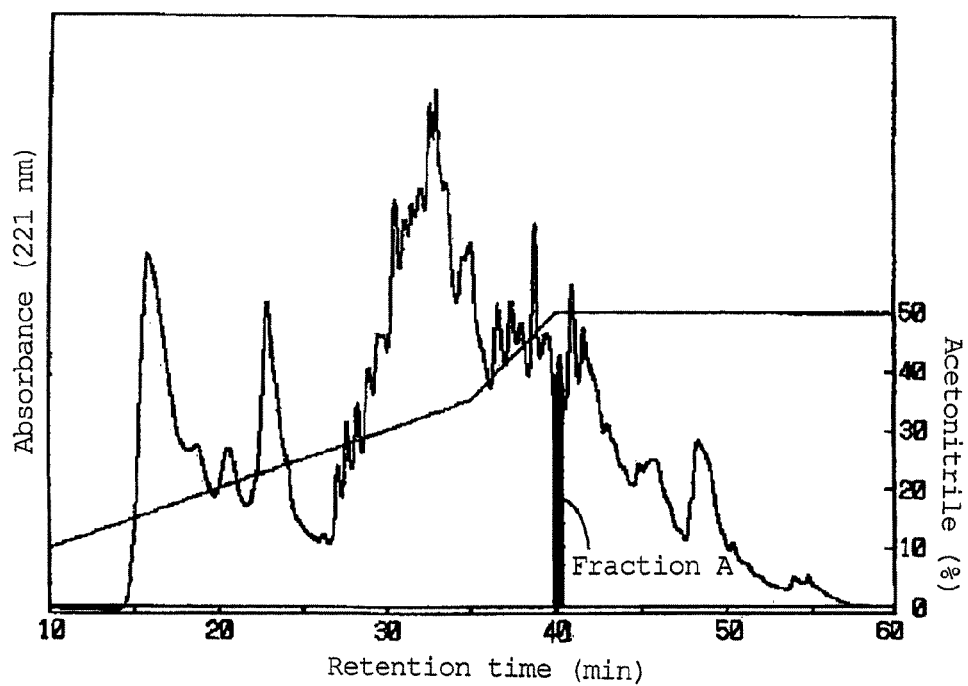
FIG. 2 shows the results (chromatogram) of reverse phase (acid) chromatography performed in Preparation Example 2 (3).
Figure 3:
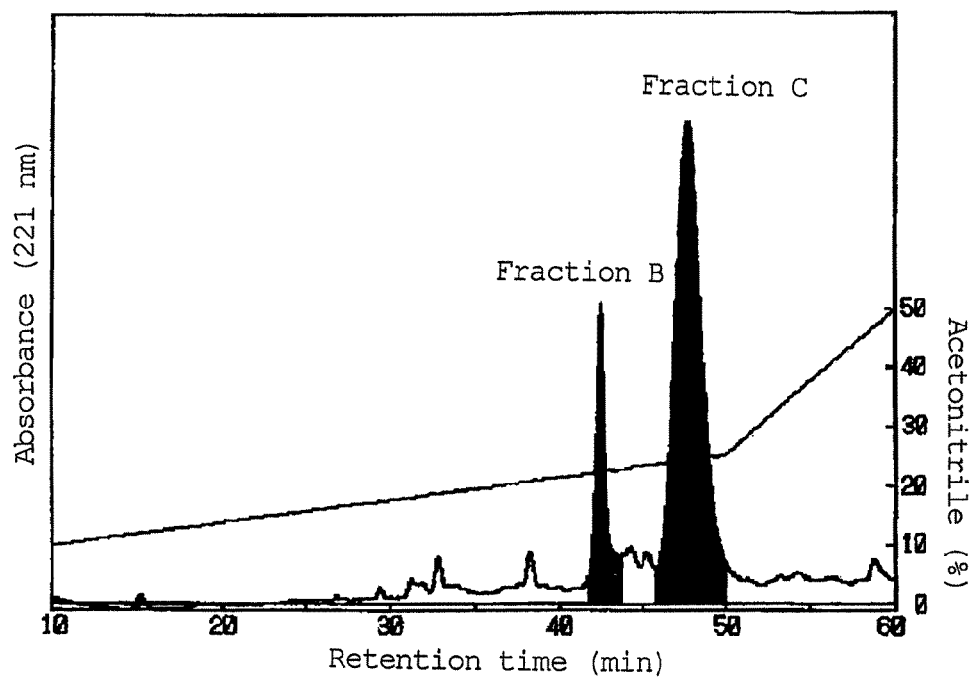
FIG. 3 shows the results (chromatogram) of reverse phase (neutral) chromatography performed in Preparation Example 2 (4).
Figure 4:
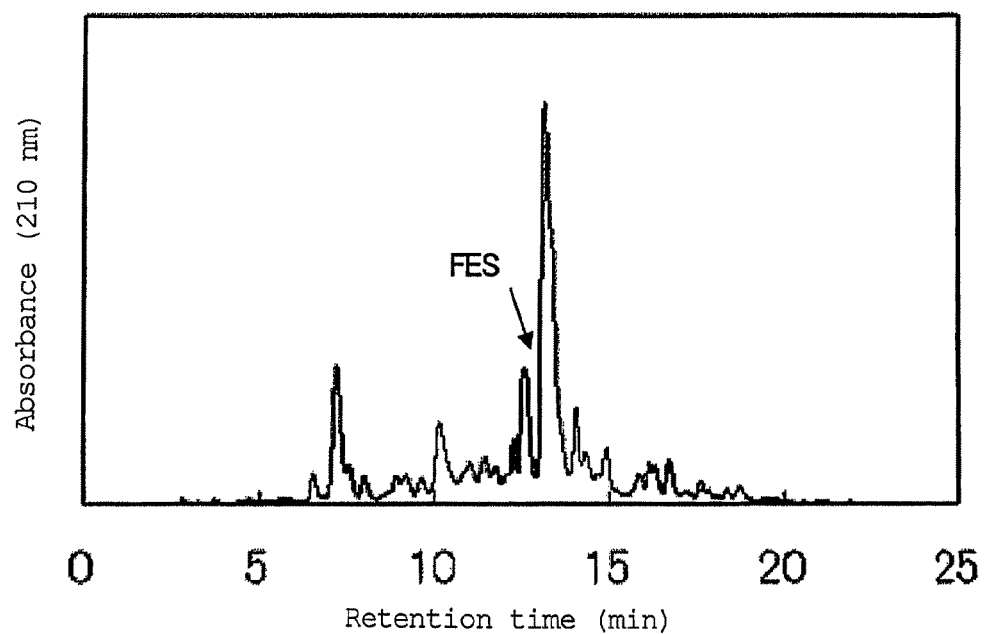
FIG. 4 shows the results (chromatogram) of reverse phase (acid) chromatography of a 5 vol. % ethanol-eluted fraction of the globin proteolysate obtained in Preparation Example 3.
Figure 5:
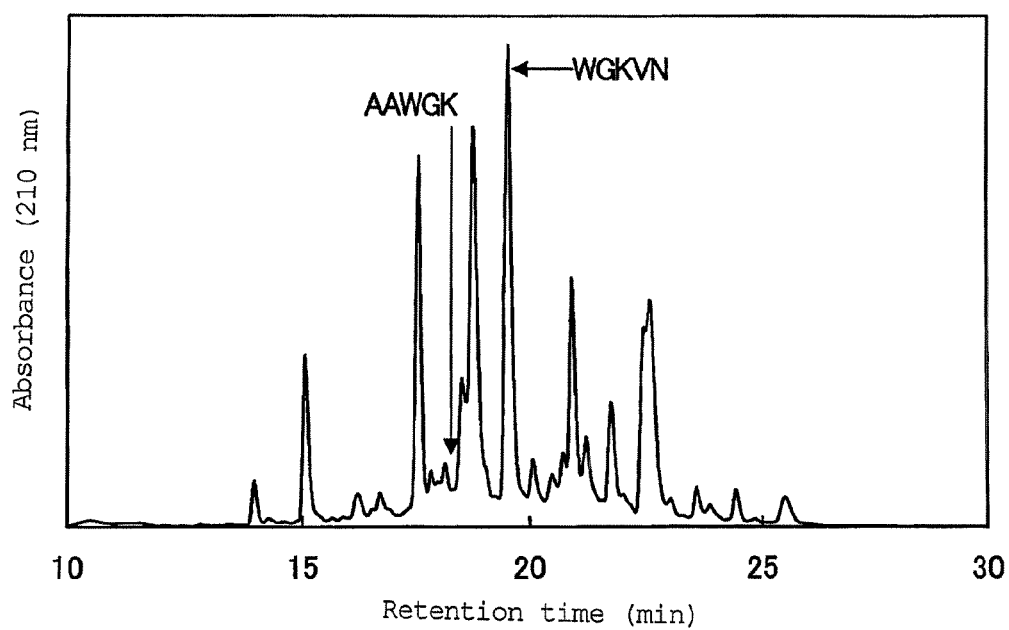
FIG. 5 shows the results (chromatogram) of reverse phase (acid) chromatography of a 15 vol. % ethanol-eluted fraction of the globin proteolysate obtained in Preparation Example 3.
Figure 6:
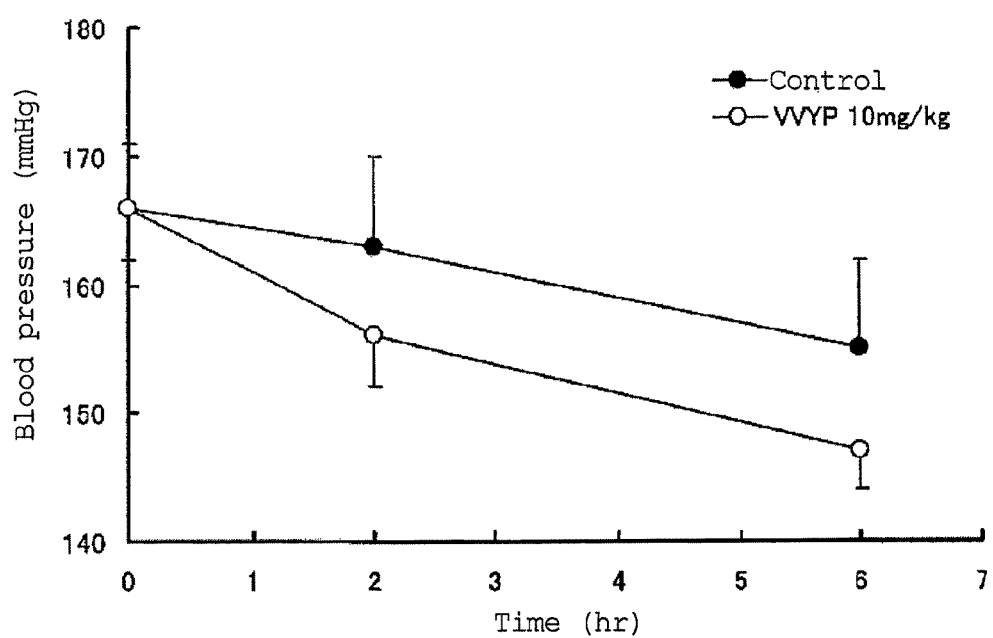
FIG. 6 shows blood pressure changes over time in spontaneously hypertensive rats orally administered with the peptide (VVYP; SEQ ID NO:1) (Experiment Example 1).
Figure 7:
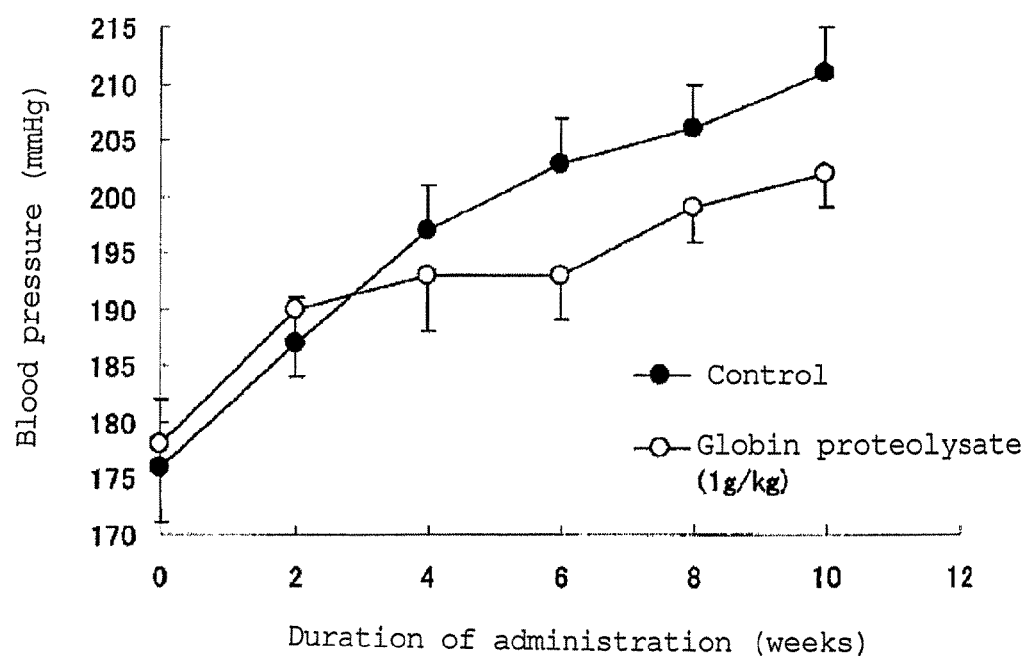
FIG. 7 shows blood pressure changes over time in spontaneously hypertensive rats orally administered with a globin proteolysate containing the peptide (VVYP; SEQ ID NO:1) (Experiment Example 2).
Figure 8:
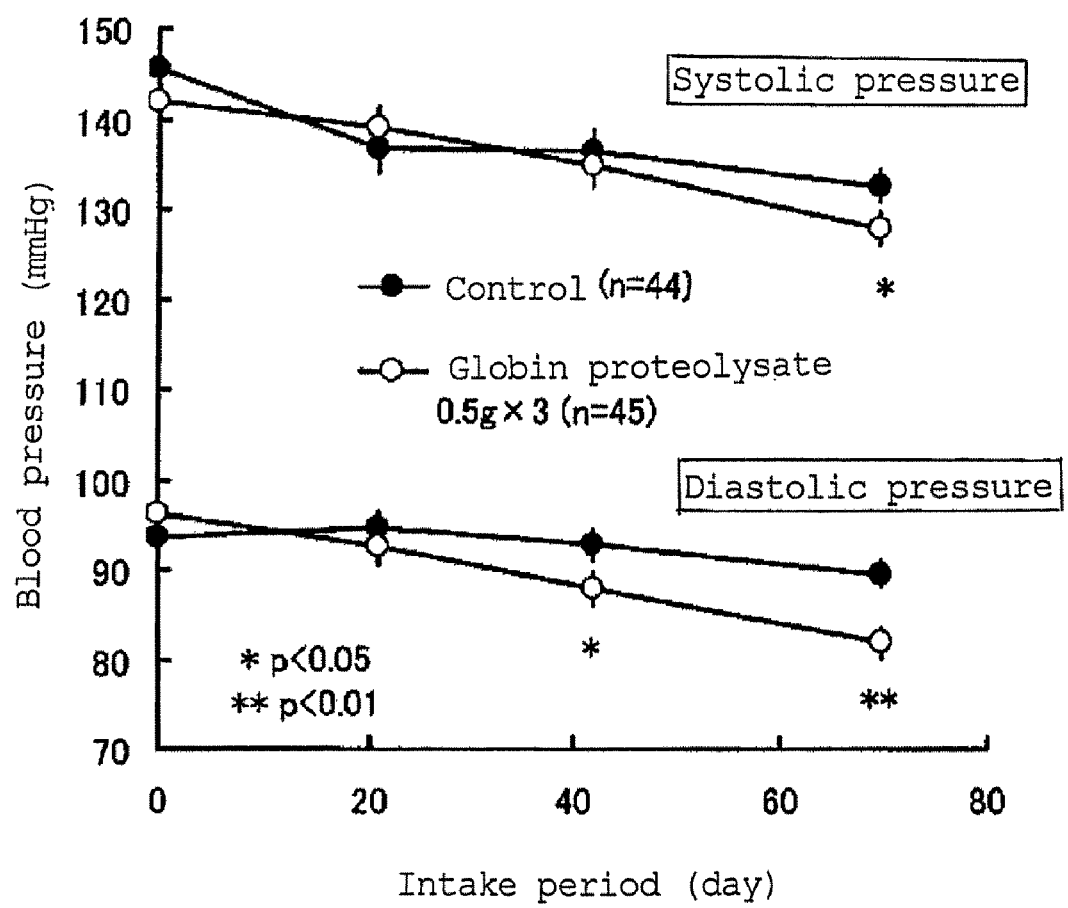
FIG. 8 shows blood pressure (systolic blood pressure and diastolic blood pressure) changes over time in mildly hypertensive human patients orally administered with a globin proteolysate containing the peptide (VVYP; SEQ ID NO:1) (Experiment Example 3).

The amino acid sequences of peptides contained in globin hydrolysates (globin proteolysates) are shown in SEQ ID: NOS. 1 to 6.

The amino acid sequence of a peptide contained in an egg white enzymatic hydrolysate is shown in SEQ ID: NO. 7.

The invention claimed is:

1. A composition comprising,
   (i) as an active ingredient, at least one peptide selected from the group consisting of Trp-Gly-Lys-Val-Asn (SEQ ID NO:2), Trp-Gly-Lys-Val (SEQ ID NO:3), and Trp-Gly-Lys (SEQ ID NO:4) or a globin proteolysate comprising at least one peptide selected from the group consisting of Trp-Gly-Lys-Val-Asn (SEQ ID NO:2), Trp-Gly-Lys-Val (SEQ ID NO:3), and Trp-Gly-Lys (SEQ II) NO:4) and
   (ii) a pharmacologically acceptable carrier or an additive.

2. The composition according to claim 1, which is orally administered to a mildly hypertensive patient.

3. The composition according to claim 1, which is administered to a hypertensive patient with a disease caused by hyperglycemia or in a pre-disease state.

4. The composition according to claim 1, which is administered by the oral route every day for a total daily dose of the peptide active ingredient of 1 to 500 mg/adult/day or a total daily dose of the globin proteolysate active ingredient of 0.1 to 5 g/adult/day.

5. The composition according to claim 1, wherein the composition is formulated for oral administration.

6. The composition according to claim 1, wherein the composition is formulated for oral administration for a total daily dose of the peptide active ingredient of 1 to 500 mg/adult/day or a total daily dose of the globin proteolysate active ingredient of 0.1 to 5 g/adult/day.

7. A peptide selected from the group consisting of Trp-Gly-Lys-Val-Asn (SEQ ID NO:2), Trp-Gly-Lys-Val (SEQ ID NO:3), and Trp-Gly-Lys (SEQ ID NO:4) or a globin proteolysate comprising at least one peptide selected from the group consisting of Trp-Gly-Lys-Val-Asn (SEQ ID NO:2), Trp-Gly-Lys-Val (SEQ ID NO:3), and Trp-Gly-Lys (SEQ ID NO:4) 4.

8. A peptide or a globin proteolysate according to claim 7, wherein the peptide or a globin proteolysate being one for use in amelioration of hypertension or prevention or treatment of a disease caused by hypertension.

9. A method of treating hypertension or a disease caused by hypertension in a subject, comprising administering to the subject the composition according to claim 1.

10. The method according to claim 9, wherein the composition is orally administered to the subject.

11. The method according to claim 9, wherein the composition is administered to a hypertensive subject having a disease caused by hyperglycemia or to a hypertensive subject in a pre-disease state.

12. The method according to claim 9, wherein the composition is orally administered to the subject daily with a total dose of the at peptide active ingredient of 1 to 500 mg/adult/day or a total daily dose of the globin proteolysate active ingredient of 0.1 to 5 g/adult/day.

* * * * *

UNITED STATES PATENT AND TRADEMARK OFFICE
CERTIFICATE OF CORRECTION

PATENT NO. : 8,394,769 B2　　　　　　　　　　　　　　　　　　　　　　　Page 1 of 1
APPLICATION NO. : 12/671953
DATED : March 12, 2013
INVENTOR(S) : Kagawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 338 days.

Signed and Sealed this

First Day of September, 2015

Michelle K. Lee
*Director of the United States Patent and Trademark Office*

```
SEQUENCE LISTING

<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Peptide found in globin hydrolysate

<400> SEQUENCE: 1

Val Val Tyr Pro
1

<210> SEQ ID NO 2
<211> LENGTH: 5
<212> TYPE: PRT
<213> ORGANISM: Artificial Sequence
<220> FEATURE:
<223> OTHER INFORMATION: Peptide found in globin hydrolysate

<400> SEQUENCE: 2

Trp Gly Lys Val Asn
1               5

<210> SEQ ID NO 3
<211> LENGTH: 4
<212> TYPE: PRT
<213> ORGANISM: Artificial Sequence
<220> FEATURE:
<223> OTHER INFORMATION: Peptide found in globin hydrolysate

<400> SEQUENCE: 3

Trp Gly Lys Val
1

<210> SEQ ID NO 4
<211> LENGTH: 3
<212> TYPE: PRT
<213> ORGANISM: Artificial Sequence
<220> FEATURE:
<223> OTHER INFORMATION: Peptide found in globin hydrolysate

<400> SEQUENCE: 4

Trp Gly Lys
1

<210> SEQ ID NO 5
<211> LENGTH: 5
<212> TYPE: PRT
<213> ORGANISM: Artificial Sequence
<220> FEATURE:
<223> OTHER INFORMATION: Peptide found in globin hydrolysate
```

```
<400> SEQUENCE: 5

Ala Ala Trp Gly Lys
1               5

<210> SEQ ID NO 6
<211> LENGTH: 3
<212> TYPE: PRT
<213> ORGANISM: Artificial Sequence
<220> FEATURE:
<223> OTHER INFORMATION: Peptide found in globin hydrolysate

<400> SEQUENCE: 6

Phe Glu Ser
1

<210> SEQ ID NO 7
<211> LENGTH: 6
<212> TYPE: PRT
<213> ORGANISM: Artificial Sequence
<220> FEATURE:
<223> OTHER INFORMATION: Peptide found in egg white
<220> FEATURE:
<221> NAME/KEY: MISC_FEATURE
<222> LOCATION: (4)..(4)
<223> OTHER INFORMATION: Xaa represents His, Lys or Arg

<400> SEQUENCE: 7

Arg Pro Leu Xaa Pro Trp
1               5
```